United States Patent

Ohtsu et al.

[11] 4,082,997
[45] Apr. 4, 1978

[54] OIL DETECTING DEVICE

[75] Inventors: Takao Ohtsu; Yukinobu Nakamura; Akira Sugimoto, all of Yokohama, Japan

[73] Assignee: Japan Gasoline Co., Ltd., Japan

[21] Appl. No.: 589,538

[22] Filed: Jun. 23, 1975

[30] Foreign Application Priority Data

Jun. 25, 1974 Japan .................................. 49-73047

[51] Int. Cl.$^2$ ....................... G01R 27/02; H01C 8/00; B01D 13/00; B01D 39/00
[52] U.S. Cl. ................................... 324/65 R; 338/225; 210/23 R; 210/96 M; 210/501
[58] Field of Search .................. 340/236; 338/225, 34, 338/35; 73/421; 210/DIG. 5, 62, 85, 86, 87, 96, 131, 501, 23; 324/65 R, 65 P

[56] References Cited

U.S. PATENT DOCUMENTS

| | | | |
|---|---|---|---|
| 3,019,904 | 2/1962 | Stecher | 210/DIG. 5 |
| 3,096,204 | 7/1963 | Spangler et al. | 210/DIG. 5 |
| 3,229,817 | 1/1966 | Pall | 210/DIG. 5 |
| 3,242,073 | 3/1966 | Guebert et al. | 210/501 |
| 3,395,802 | 8/1968 | Rosaen | 210/131 X |
| 3,462,362 | 8/1969 | Kollsman | 210/23 |
| 3,719,936 | 3/1973 | Daniels et al. | 340/236 |
| 3,847,810 | 11/1974 | Tulumello | 210/96 |
| 3,860,517 | 1/1975 | Shema et al. | 210/62 |
| 4,008,619 | 2/1977 | Alcaide et al. | 73/398 C |

Primary Examiner—Frank A. Spear, Jr.
Assistant Examiner—D. R. Sadowski
Attorney, Agent, or Firm—Spensley, Horn & Lubitz

[57] ABSTRACT

The present invention provides an oil detecting element capable of accurately detecting oil floating on water. The oil detecting element comprises a water-repellent, oil-passing filtering member for preventing water coming into the element. Oil can be detected by detecting change in electric resistance of a conductive particle layer due to its contact with oil arriving through the member. According to an embodiment of the invention, the water-repellent, oil-passing filtering member is impregnated with a material which is toxic to water life such as algae and shells to prevent settling of these water life on the surface of the element and thereby to prolong the life of the element. Examples of an oil detector incorporating the oil detecting element and including an electrical circuit which detects change in electric resistance of the element upon its contact with oil and actuates a suitable alarming device such as a buzzer are described.

4 Claims, 5 Drawing Figures

OIL DETECTING DEVICE

This invention relates to an oil detecting element and an oil detector incorporating the oil detecting element suitable for detecting oil floating on water such as oil floating on a river, lake, or sea, or sewer in the oil refineries, chemical factories etc. and oil leaking in an underground pipeline.

Various proposals have been made for detecting water pollution due to floating oil or oil leakage in a pipeline. There is, for example, a proposal for detecting oil leakage in a pipeline system utilizing an electrically conductive organic material. According to this proposal, the conductive organic material is formed by mixing carbon black into an organic material such as natural rubber and leaking oil is detected by change in electric resistance of the conductive organic material which occurs when the leaking oil comes into contact with the material. This device is disadvantageous, however, in that the conductive organic material which is formed by mixing a powdered conductive material into an organic material and thereafter solidifying them together is not sufficiently permeable to oil and, accordingly, response to the change in electric resistance at the time of contact between oil and the material is so slow and the value of change is too small that application of this prior art device is limited to detection of oil leakage in a pipeline where a large amount of leaking oil is present. Furthermore, the prior art device is defective in that no consideration is given to elimination of water which tends to contact the detector so that conductivity of the conductive organic material tends to increase when water comes into contact with the material notwithstanding the fact that the material is in contact with oil. This apparently offsets change in electrical resistance with a resulting inaccuracy in detection.

As to detection of oil on water in rivers and seas, devices such as utilizing reflection of light have been proposed and used. These devices depending upon optical methods require a relatively complicated and large construction and the manufacturing cost is inevitably high.

It is, therefore, an object of the present invention to provide an oil detecting element capable of detecting oil on water with a high degree of response and sensitivity.

It is another object of the invention to provide an oil detecting element capable of preventing deposition of water life such as algae and shells on the surface of the element thereby to ensure a satisfactory oil detecting function of the element over a long period of time.

It is still another object of the invention to provide an oil detector which produces a signal when resistance of the oil detecting element has changed in excess of a predetermined value and actuates an alarming device by means of this signal.

These and other objects and features of the invention will become apparent from the description of preferred embodiments made hereinbelow with reference to the accompanying drawings in which.

DESCRIPTION OF THE INVENTION

Figure 1:
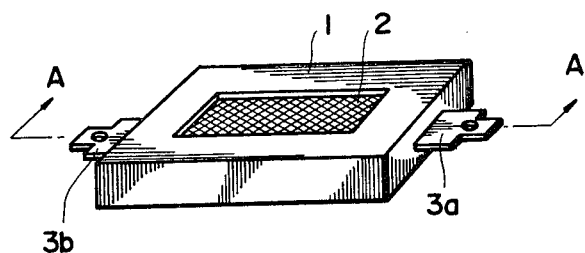
FIG. 1 is a perspective view of a preferred embodiment of the oil detecting element according to the invention.
Figure 2:
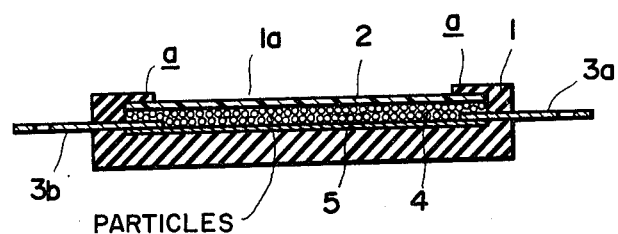
FIG. 2 is a sectional view of the oil detecting element shown in FIG. 1.

Referring first to FIGS. 1 and 2, the oil detecting element comprises a casing 1 which has an opening 1a on one side thereof. A filtering member 2 made of water-repellent, oil-passing material is mounted in this opening 1a. The casing 1 consists of a rigid or soft non-conductive material such as plastics. The casing 1 is bonded or otherwise connected watertight to the member 2 at an end portion a thereof to prevent water from coming into the opening 1a. The water-repellent, oil passing filtering member 2 is made of a material which passes oil and repels water such as synthetic resin filaments or natural fibre coated with resin. Accordingly, water is prevented from coming into the casing 1 and only oil passes through the member 2.

In the opening 1a, a conductive particle layer 4 is provided on the rear inner side of the member 2. This conductive particle layer 4 is provided at opposite ends thereof with electrodes 3a and 3b which project outwardly from the casing 1 and are used as connecting terminals. As the conductive particles of the layer 4, particles of a suitable conductive materials such, for example, as metals, metal oxides and carbon. The conductive particle layer may be formed either by sealing the conductive particles in the opening 1a or by coating a base member 5 made of a suitable insulating material with the conductive particles. The layer 4 may also be formed by coating the rear surface of the member 2 with the conductive particles. The conductive particle layer need not be a thick one but a layer in which each particle is in contact with an adjacent particle between the electrodes 3a and 3b will suffice. The layer 4, however, should preferably be in close contact with the above described member 2.

If no oil exists but only water is present about the casing 1, water is interrupted by the water repellent member 2 and, accordingly, electric resistance of the conductive layer 4 composed of the conductive particles which are in mutual contact between the electrodes 3a and 3b does not change but remains at a predetermined low value.

If oil exists about the casing 1, this oil passes through the member 2 into the conductive layer 4. Thus, the oil comes into contact with the conductive particles and is interposed between the particles. This causes electric resistance of the conductive particle layer 4 to increase. Accordingly, existence of oil can be detected by measuring the value of electric resistance between the electrodes 3a and 3b by suitable means.

It should be noted that the layer 4 is in the form of particles so that oil rapidly reaches between the particles. Accordingly, the oil detecting element according to the invention sharply responds to an extremely small quantity of oil, e.g. in the order of few μl, and produces a relatively large change in the value of electric resistance. A result of an experiment which was conducted by introducing 100 μl of Agha jari crude oil in the inventive oil detecting element shows that resistance increased from an initial value of 6.8 to 80 KΩ in a matter of few seconds. It will be understood from this result that the inventive oil detecting element has sufficiently high response characteristics and sensitivity and change in resistance is remakably large. The value of resistance further increases as time elapses after the initial contact between oil and the conductive particle layer 4. It will be noted, therefore, that the oil detecting element according to the invention presents a sufficiently large change in electric resistance at the initial contact with oil and a still larger change after a lapse of several seconds. This enables the oil detecting element to perform oil detection immediately upon its initial contact with oil.

A material which has a large water repelling property, e.g. polyflon or silicon resin, will be particularly useful as the member 2 in detecting oil floating on water which has a relatively great conductivity such as sea water.

Figure 3:
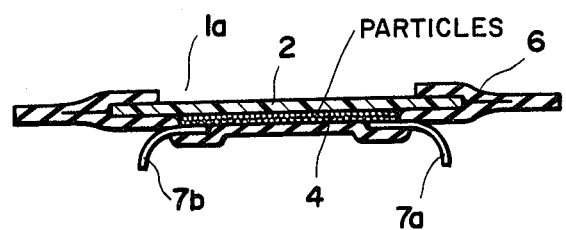
FIG. 3 is a sectional view of another embodiment of the oil detecting element according to the invention.

FIG. 3 shows another embodiment of the oil detecting element according to the present invention. This figure is a sectional view of the oil detecting element substantially constructed in the form of a sheet. A conductive particle layer 4 is coated on the rear surface of a water-repellent member 2 and this member 2 is enclosed watertight in a sheet 6 which is made of a heat melting material. The sheet 6 has an opening 1a in which the outer surface of the member 2 is exposed. The conductive particle layer 4 is provided at opposite ends thereof with electrodes 7a and 7b consisting of pieces of metal foil. These electrodes 7a and 7b are bonded to the layer 4 and are projecting out of the lower surface of the sheet 6. This embodiment is a compact construction compared with the previously described embodiment and the member 2 and the conductive particle layer 4 used in the previously described embodiment may be effectively used in the present embodiment.

In case wherein the oil detecting element is disposed in water for a long time, water life such as algae and shells tend to settle and grow on the surface of the oil detecting element with a resultant lowering of detecting efficiency. It is therefore necessary in such cases to provide means for preventing settling of water life on the surface of the oil detecting element. For this purpose, another embodiment of the present invention uses a water-repellent member containing a material which is toxic to the water life. As this material contained in the member, any material among organic chlorides may be used as long as it is poisonous to the water life and hard to dissolve in water. For example, pentachlorophenol-2,3-dichloro-1,4-nephthoquinone may be effectively used as this material.

It should be noted that oleophilic and water-repellent properties of the water-repellent member are not hampered by including the above described toxic material in the member. The toxic material must be hard to dissolve in water because otherwise the material will be rapidly dissolved by water and will not be able to prevent settling of the water life on the surface of the oil detecting element. If the material is hard to dissolve in water, it will dissolve only gradually and prevent settling of the water life which tend to settle on the surface of the oil detecting element. Contents of the toxic-material in the order of 0.5-5 wt % in the entire member 2 will be sufficient to preventing settling of the water life.

Figure 4:
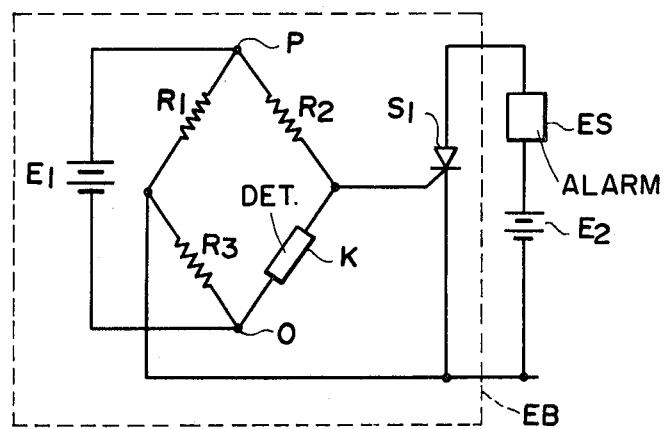
FIG. 4 is a circuit diagram showing an example of oil detector incorporating the oil detecting element.
Figure 5:
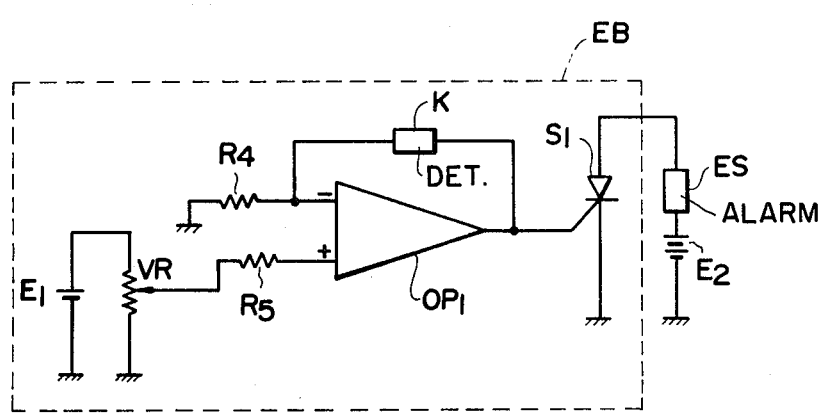
FIG. 5 is a circuit diagram showing another example of oil detector incorporating the oil detecting element.

FIGS. 4 and 5 show examples of an oil detector which employs one of the above described oil detecting elements. The oil detector comprises an oil detecting element K, a detection circuit EB which detects change in resistance of the oil detecting element K and produces a detection signal and an alarming circuit ES which is actuated by this detection signal. In the example shown in FIG. 4, a bridge circuit is used as the detection circuit EB. More specifically, resistors $R_1$-$R_3$ and the oil detecting element K are connected in bridge connection, a power source $E_1$ is connected between connection points P and O, and a connection point between the resistor $R_2$ and the oil detecting element K is connected to the gate of a silicon control rectifier $S_1$. The alarming circuit ES and a power source $E_2$ are connected in series to the silicon control rectifier $S_1$. As the alarming circuit ES, a known circuit such, for example, as one for actuating a buzzer or lighting a lamp or a transmitter may be effectively employed. The alarming curcuit ES is provided for informing a watchman in a remote place of detection of oil on water.

Assume that the oil detecting element K has detected oil on water and its value of resistance has sharply increased. Since in this case a positive voltage is applied to the gate of this silicon control rectifier $S_1$, the silicon control rectifier $S_1$ conducts and thereby actuates the alarming circuit ES to inform the watchman of the detection of oil.

FIG. 5 shows another example of the oil detector incorporating the oil detecting element. A differential amplifier $OP_1$ constructed of an integrated circuit is used as a detection circuit EB, an oil detecting element K is provided in a feed-back circuit of this differential amplifier $OP_1$. These circuits as a whole constitute a non-phase-inverting amplifier. In this example also, values of resistance of input resistors $R_4$ and $R_5$ are selected at such ones that the amplifier $OP_1$ will not emit a detection signal when no oil is detected. Reference characters VR designate a variable resistor provided for adjusting sensitivity of the oil detector. When the oil detecting element K has detected oil, the value of resistance thereof increases thereby causing the amplification factor to increase. This produces a detection signal of a positive voltage which brings the silicon control rectifier $S_1$ into conduction. Subsequent operation of this oil detector is the same as the one which has been described with reference to the example shown in FIG. 4.

In this oil detector, voltage across the oil detecting element K can be of a relatively small value (e.g., 0.3V). Accordingly, this oil detector is advantageous in that no electrolysis takes place even if water should come into the oil detecting element and therefore the oil detector can enjoy a longer life.

Some specific examples of the oil detecting element according to the invention will now be described.

EXAMPLE 1

Craphite particles were coated uniformly on one side of a water-repellent member having dimensions of 1 by 4 cm. The graphite particles serve as the conductive particle layer 4. Electrodes were connected to opposite ends of this coated layer 4. Thus, the oil detecting element as shown in FIGS. 1 and 2 was constructed. Three specimens A, B and C of this type of oil detecting element were made by employing different water-repellent materials as shown in Table I to be described later.

Each of the specimens of the oil detecting element was attached to a buoy in such a manner that the surface of the oil detecting element (i.e. the surface of the water-repellent member) would intersect at right angles with the surface of water and this buoy was floated on one end region of a seawater pool of 1 by 4 m in such a manner that about half of the surface of the oil detecting element would submerge below the surface of water.

Crude oil of about 10 ml was quietly dropped on the other end region of the seawater pool.

A film of oil formed on water gradually spread until it reached the surface of the oil detecting element attached to the buoy. Change in values of resistance of the oil detecting element was measured after the oil film reached the surface of the element. Results of the measuring are shown in the following Table I.

Table I

| element | material of member 2 | Initial resistance | resistance after 10 seconds |
|---|---|---|---|
| A | unwoven cloth of polyflon | 7.8 KΩ | 115 KΩ |
| B | unwoven cloth of polyethylene | 12.0 | 151 |
| C | filter paper (No. 5C) treated with silicon | 7.4 | 168 |

EXAMPLE 2

An oil detecting element which is identical with the specimen A of the above described first example was used with kerosene instead of crude oil. The value of resistance of this element initially was 8.3 KΩ and it increased to 21 KΩ when 10 seconds elapsed after the oil film reached the surface of the element.

EXAMPLE 3

A test similar to the first example was conducted by using a specimen which was identical with the above described specimen A. This test was conducted in fresh water instead of seawater. The resistance changed from the initial value of 8.0 to 120 KΩ when 10 seconds elapsed after the oil film reached the surface of the element.

EXAMPLE 4

Organic chlorides shown in the following Table II were dissolved in a suitable organic solvent such as alcohol or benzene to make solution of about 2%. A member made of a polyflon unwoven cloth with dimensions of 1 by 4 cm was dipped in the solution for about one to five minutes and it was dried thereafter. This operation was repeated two or three times to make water-repellent members respectively containing one of the organic chlorides. Content of the organic chloride in the filter was about 1 wt %. Specimens of the member were soaked in a beaker in which a heavy oil film was formed on water to examine permeability of water and that of oil. Then, the specimens of member which had already been treated with the above described chemical preparations were uniformly coated on one side thereof with graphite particles and electrodes were connected at opposite ends of the coated layer to constitute an oil detecting element. The oil detecting element was attached to a buoy and a test was conducted to detect oil floating on the sea. Simultaneously, state of settling of algae was observed. Results of these tests are shown in the following Table II:

Table II

| preparation with which water-repellent member was treated | Water-repellent member | | initial resistance | 2 days after floating on seawater resistance 10 secs. after contact with oil | 20 days after floating on seawater resistance 10 secs. after contact with oil | settling of algae |
|---|---|---|---|---|---|---|
| | water repellent property | oleophilic property | | | | |
| no treatment | Yes | Yes | 7.8$^{KΩ}$ | 121$^{KΩ}$ | not detectable | ++ |
| dichlorobenzene | Yes | Yes | 8.0 | 118 | 120$^{KΩ}$ | + |
| 2-benzoyl-1,3-dichloropropane | Yes | Yes | 6.8 | 129 | 131 | — |
| 2,3-dichloronaphtoquinone | Yes | Yes | 7.2 | 110 | 118 | — |
| pentachlorophenol | Yes | Yes | 8.3 | 112 | 116 | — |

The oil detecting element according to the present invention is not limited to the construction and shape shown in the accompanying drawings but any construction or shape may be employed as long as the water-repellent filter passes oil only to allow it to come into contact with the conductive particle layer with a resultant change in electric resistance of the element.

The oil detecting element and the oil detector incorporating the oil detecting element according to the invention may be employed in all regions including rivers, lakes, seas, sewer in the oil refineries etc. and underground pipelines. If, for example, the oil detecting element or the oil detector is to be used for detecting exhaust oil floating on the sea, several pieces of the oil detecting element or the oil detector are disposed in desired detection places such as an entrance of a bay. The oil detecting elements or the oil detectors should be floated on water in such a manner that the water-repellent member will easily come into contact with the floating oil. The oil detecting elements or the oil detectors thus provided on water are expected to detect oil rapidly and prove very useful for preventing water pollution which will cause a great damage to sea-products etc.

If the inventive oil detecting element or oil detector is used in an underground pipeline, it will accurately detect the smallest quantity of leaking oil without being affected by water coexisting with oil. It will be understood that the oil detecting element or oil detector can detect not only mineral oils but other kinds of oils including animal and plant oils.

What is claimed is:
1. An oil detecting element comprising:
   a container having one opening therein;
   a water repellent, oil passing filter member closing said opening; and
   an electrically conductive particle layer made of particles which are formed from a material selected from the group consisting of carbon, metal oxides and metal provided in said container whereby when said particle layer is soaked with oil which has passed through said filtering member, the oil comes in contact with the conductive particles and interposes between particles and causes the electrical resistance of said particle layer to increase.
2. An oil detecting element as defined in claim 1 wherein said filtering member is impregnated with pentachlorophenol-2,3-dichloro-1,4-naphthoquinone.

3. An oil detecting element as defined in claim 1 wherein said container comprises a sheet of a heat melting material which encloses in hermetically seals said filter member and said conductive particle layer therein and has an opening in which the outer surface of said member is exposed, said conductive particle layer being coated on the inner surface of said filter member.

4. An oil detecting element as defined in claim 1 wherein said container comprises a casing and an insulating sheet having an opening therein and having said filter member and said conductive particle layer stacked on said insulating sheet, said insulating sheet hermetically sealing said filter member and conductive particle layer in said casing with on an outer surface of said filter member being exposed in said opening.

* * * * *